United States Patent [19]

Nazzaro-Porro

[11] Patent Number: 5,385,943

[45] Date of Patent: Jan. 31, 1995

[54] USE OF TOPICALLY APPLICABLE PREPARATIONS FOR TREATMENT OF PRESBYDERMA

[75] Inventor: Marcella Nazzaro-Porro, Rome, Italy

[73] Assignee: Schering Aktiengesellschaft, Berlin and Bergkamen, Germany

[21] Appl. No.: 43,955

[22] Filed: Apr. 7, 1993

Related U.S. Application Data

[63] Continuation of Ser. No. 892,878, Jun. 3, 1992, abandoned, which is a continuation of Ser. No. 604,403, Oct. 24, 1990, abandoned, which is a continuation of Ser. No. 330,046, Mar. 29, 1989, abandoned.

[30] Foreign Application Priority Data

Mar. 30, 1989 [DE] Germany .............................. 3811081

[51] Int. Cl.⁶ .............................................. A61K 31/19
[52] U.S. Cl. ...................................... 514/574; 514/859; 514/863
[58] Field of Search ................ 514/557, 574, 859, 863

[56] References Cited

U.S. PATENT DOCUMENTS

| | | | |
|---|---|---|---|
| 4,294,852 | 10/1981 | Wildnauer et al. | 424/317 |
| 4,386,104 | 5/1983 | Nazzaro-Porro | 424/317 |
| 4,661,519 | 4/1987 | Shiga et al. | 514/547 |
| 4,767,750 | 8/1988 | Jacquet et al. | 514/159 |

OTHER PUBLICATIONS

CA 64:14841a (1966) LaVeen, H. H. et al.
CA 77:150684e, Rubio, M. J. (1972).
CA 82:61765t, Carman, W. T. (1975).

*Primary Examiner*—Gary E. Hollinden
*Attorney, Agent, or Firm*—Millen, White, Zelano, & Branigan

[57] ABSTRACT

The invention relates to the use of topically applicable preparations containing alpha,omega-n-alkanedicarboxylic acids with 7 to 13 carbon atoms, their physiologically compatible salts or their esters cleavable by means of enzymes of the skin, as active ingredients for treatment of keratoses.

21 Claims, No Drawings

USE OF TOPICALLY APPLICABLE PREPARATIONS FOR TREATMENT OF PRESBYDERMA

This is a continuation of application Ser. No. 07/892,878 filed Jun. 3, 1992, ABN, which is a continuation of 07/604,403, filed Oct. 24, 1990, ABN, which is a continuation of 07/330,046 filed Mar. 29, 1989, abandoned.

BACKGROUND OF THE INVENTION

It is known that topically applicable preparations, which contain as an active ingredient alpha,omega-n-alkanedicarboxylic acids with 7 to 13 carbon atoms, their physiologically compatible salts or their esters cleavable by means of enzymes of the skin, can be used for treatment of some special skin diseases. Thus it is described in U.S. specification 4,386,104 that preparations, which contain such carboxylic acids as active ingredient, are suitable for treatment of acne. In European patent application 0229654 it is described that such preparations are suitable for treatment of inflammatory and infectious dermatoses. The use of such preparations for treatment of rosacea is claimed in German patent application 36 23 862. U.S. specification 4,661,519 describes agents for treatment of acne, which contain as active ingredients esters of alpha,omega-n-alkanedicarboxylic acids with 7 to 13 carbon atoms, such esters being easily cleavable with enzymes of the skin.

SUMMARY OF THE INVENTION

It has now been found that such preparations surprisingly can also be used with good results for the treatment of presbyderma. By the concept of presbyderma according to the invention are to be understood changes caused by old age in integumentary appendages. The condition is equivalent to the German term "altershaut" meaning old skin, and is known in, e.g., Pugliese, "Concepts in Aging and the Skin", *Cosmetics and Toiletries*, Vol. 102, pp. 19–44 (1987) and in Fenske et al., "Structural and Functional Changes of the Normal Aging Skin", *J. Am. Acad. of Dermatology*, Vol. 15, pp. 571–585 (1986).

It is known that the skin, with increasing age, tends to become drier, more wrinkled, more sallow, less elastic and mechanically less resilient.

With increasing age, a multiplicity of pigmented and nonpigmented spots occur on the skin, such as, for example, brown, gray or sallow old age spots, comedones, enlargements of sebaceous glands, keratoderma and persistent or permanent vascular dilations, especially also of the cutaneous vessels, as a result of prolonged effect of the sun. Very often corns, calluses and onychogryposes occur on the feet with increasing age as a result of chronic mechanical stress.

Although these abnormal changes of the skin from the viewpoint of their origin are completely different from the above-mentioned skin diseases, i.e., acne, rosacea, etc., in a surprising way they can be very successfully used with topically applicable preparations, containing carboxylic acids as active ingredients. Suitable dicarboxylic acids according to the invention include hydrocarbons, preferably aliphatic, preferably saturated, especially those which are alpha,omega-n-alkanedicarboxylic acids with 7 to 13 carbon atoms, their physiologically acceptable salts or their esters cleavable by means of skin enzymes. This effect was not possible by means of previously known methods of treatment to a satisfactory degree.

It was already mentioned that such topically applicable preparations and their production are known. But, on the other hand, it is also possible to make new preparations suited to the special requirements of presbyderma (Am. Perfumer 77, 1962, 49; Z. Gerontol. 1976, 377; Drug Cosmet. Ind. 119, 1976, 54; Bristol Myers Nutr. Symp. 1986, 35).

The production of such topical preparations takes place in the usual way by the active ingredients with suitable additives being converted into the desired application form such as, for example, a solution, a milk, a lotion, a cream, an ointment or a paste. In the preparation thus formulated the concentration of active ingredient depends on the form of application. Preferably a concentration of 5 to 30% by weight of active ingredient is used.

The milk, lotion or cream (oil/water emulsions) and the ointment (water/oil emulsions) can be produced in the standard way by use of standard emulsifiers (Kirk Othmer: Encyclopedia of Chemical Technology, 3rd edition, 1979; John Wiley & Sons, New York, Vol 8, pages 900–930, and Dr. Otto-Albrecht Neumueller: Roempps Chemie Lexikon, 7th edition, 1973; Franckh'sche Verlagshandlung Stuttgart, pages 1009–1013). The waxes. emulsifier and other additives are the same as standardly used (Dr. Otto-Albrecht Neumueller: Roempps Chemie Lexikon, 7th edition, 1973; Franckh'sche Verlagshandlung Stuttgart, pages 1427 and 1428).

The topical preparation according to the invention can consist of hydrophilic and/or lipophilic active ingredients, fatty phase, oil/water emulsifier, aqueous phase and preservatives.

As hydrophilic and/or lipophilic additives, moisture-holding factors (hydrocomplexes), such as, for example, propylene glycol, glycerol, polyethylene glycols, vital complexes (such as, for example, placenta extracts), enzymes, herbal extracts (such as, for example, hamamelis extract or chamomile extract) or proteins (such as, for example, collagen) can be used. As an oily phase or as a fatty phase in the oil/water emulsion suitable agents are hydrocarbons such as, for example, squalene, vaseline, paraffins or stearin, or waxes, such as, for example, beeswax or animal or vegetable oils, such as olive oil, peanut oil, fine bone oil, almond oil, jojoba oil, lanolin or sunflower oil. Suitable oil/water emulsifiers are, for example, stearyl alcohol, polyoxyethylene stearates (such as, for example, MYRJ$^{(R)}$), complex emulsifiers (such as, for example, Amphoterin$^{(R)}$) and sorbitan fatty acid esters (such as, for example, Tween 80$^{(R)}$), carboxyvinyl polymers (such as, for example, Carbopol$^{(R)}$), fatty alcohols such as, for example, cetyl alcohol, myristyl alcohol or mixed esters (such as, for example, Dehymuls$^{(R)}$). The aqueous phase can additionally also contain buffer substances, such as, for example, disodium salt of ethylenediamine-N,N,N'N'-tetraacetic acid and preservatives, such as benzoic acid, chloroquinaldol, Parabens or benzalkonium chloride.

The emulsion additionally is mixed with active ingredient that is preferably micronized (grain size, preferably 1 to 20 microns) and optionally also with aromatic substances such as, for example, those of the Cremates$^{(R)}$ series and stirred to homogeneous distribution.

Concentrations in other compositions will be analogous and can be readily determined in fully conventional fashion. Typically, such compositions will be administered directly to the affected skin of a mammal, including humans, as appropriate, most typically 1-2 times per day.

Alpha,omega-n-alkanedicarboxylic acids with 7 to 13 carbon atoms, their physiologically compatible salts or their esters cleavable by means of skin enzymes are used as active ingredients.

The dicarboxylic acids used according to the invention include especially pimelic acid, suberic acid. azelaic acid (1,7-heptanedicarboxylic acid), sebacic acid, 1,9-nonanedicarboxylic acid, 1,10-decanedicarboxylic acid and 1,11-undecanedicarboxylic acid.

The dicarboxylic acid esters cleavable by means of skin enzymes include, for example, the 2,3-dihydroxypropyloxy esters of these substances. Such clearable esters would be known to or easily determinable with only routine experimentation by one ordinary skill in the art.

The physiologically compatible salts include alkali metal salts, such as sodium and potassium salts, further salts with basic amino compounds and organic amines, such as, for example, arginine, lysine or N-methylglucamine. These are well known in the art and can be fully conventionally prepared, as per, e.g., U.S. Pat. No. 4,661,559 noted above.

Azelaic acid is used as the dicarboxylic acid in a preferred embodiment.

In addition to the esters and salts of carboxylic acids, any carboxylic acid derivative which generates an acid radical through cleavage by skin enzymes, dissociation or ionization on the skin would be effective in the invention.

It is often advantageous additionally to add to the agents according to the invention about 1 to 4% by weight of a keratolytically active substance, such as, for example, salicylic acid or resorcinol relative to the total weight of the agent.

The following embodiment serves to explain the invention in greater detail.

Without further elaboration, it is believed that one skilled in the art can, using the preceding description; utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding application German P 38 11 081.4, filed Mar. 30, 1988, are hereby incorporated by reference.

EXAMPLE 17 patients with various changes of the facial skin caused by old age and 4 patients with abnormalities of the extremities caused by old age were treated twice a day with a cream containing:

|  | % by weight |
| --- | --- |
| Azelaic acid | 20.0% |
| Benzoic acid | 0.1% |
| Salicylic acid | 2.0% |
| Ascorbic acid | 1.0% |
| Glycerol monostearate | 2.0% |
| Cetyl alcohol | 3.0% |
| Polyethylene (20) sorbitan monoaleate | 5.0% |
| Sodium lauryl sulfate | 10.0% |
| Ethanolamine lauryl sulfate | 1.0% |
| Olive oil | 2.0% |
| Bidistilled water - produce according to DE-A 36 23 862 | 53.9% |

After 6 months treatment the cream was applied only once per day or sporadically over a long period.

For documentation of the treatment results the body parts were photographed before, during and after the treatment.

Detailed information is given in the following table on the patients treated.

TABLE

| Patient No. | Patient's initials | Start of Treatment | Age at Treatment | Sex | Last Treatment |
| --- | --- | --- | --- | --- | --- |
| 1 | Z.M. | 11/21/77 | 55 | F | 10/9/87 |
| 2 | R.M. | 10/8/82 | 70 | F | 1/14/88 |
| 3 | B.A. | 10/9/80 | 81 | F | 12/19/80 |
| 4 | C.M. | 1/5/84 | 63 | F | 1/18/88 |
| 5 | D.P. | 6/9/87 | 49 | F | 1/18/88 |
| 6 | S.T. | 5/24/85 | 66 | F | 1/12/88 |
| 7 | B.C. | 3/4/85 | 58 | M | 1/12/88 |
| 8 | O.Q. | 10/27/83 | 66 | M | 1/20/88 |
| 9 | M.M. | 5/29/85 | 71 | F | 10/9/87 |
| 10 | F.M. | 5/10/83 | 56 | F | 1/12/88 |
| 11 | G.L. | 5/14/87 | 65 | M | 2/11/88 |
| 12 | L.L. | 9/19/86 | 54 | F | 1/12/88 |
| 13 | S.C. | 5/24/85 | 65 | F | 1/29/88 |
| 14 | B.P. | 3/12/85 | 59 | M | 2/11/88 |
| 15 | D.P. | 11/8/83 | 72 | M | 12/10/87 |
| 16 | G.G. | 6/27/85 | 79 | M | 2/11/88 |
| 17 | D.P. | 4/20/85 | 63 | M | 2/9/88 |
| 18 | M.V. | 11/26/85 | 48 | F | 2/12/88 |
| 19 | Z.F. | 9/10/82 | 64 | F | 12/10/87 |
| 20 | P.C. | 6/26/82 | 56 | M | 7/29/87 |
| 21 | A.M. | 9/22/87 | 61 | F | 1/18/88 |

M = male
F = female

Patients 1 to 4 suffered from a lentigo maligna. It was shown that in the case of this disease a healing could not only be achieved but also unaffected areas of the skin, if they were regularly treated with the cream, in comparison with untreated parts of the skin, showed a very distinctly improved condition. After treatment they were substantially more elastic, smoother, less wrinkled and no longer appeared sallow but pink. Cornifications (keratoses) and other spots caused by effect of the sun were completely or almost completely eliminated after treatment was completed.

Patients 5 to 11, before treatment, had skin areas with obstinate vascular dilation, especially those of the skin vessels close to the surface (vasodilations and telangiectasias caused by old age). These skin anomalies also were able to be eliminated entirely or largely by the treatment. Additionally in patients 8 and 11 large comedones and sebaceous enlargements (sebaceous hyperplasias) were able to be eliminated by treatment. Good to very good treatment results were also obtained in those patients who had keratoses caused by prolonged exposure to the sun (patients 12 to 16), seborrhoeic dermatoses (17), calluses (patient 18), eczemas on the hand and foot (patients 18 and 19) as well as curvature of the toenails (patients 20 and 21).

The very distinctly improved condition of the treated skin parts observed in patients 1 to 4 was also observed in the other patients, whose skin seemed to be "rejuvenated."

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method of treating keratoses in a patient in need of such treatment comprising topically administering to the affected skin of the patient an effective amount of a alpha,omega-n-$C_{7-13}$-alkanedicarboxylic acid, an ester thereof cleavable by skin enzymes or a pharmacologically acceptable salt thereof.

2. A method of claim 1, wherein said acid, ester or salt is administered in a topical formulation further comprising a pharmaceutically acceptable carrier.

3. A method of claim 2, wherein said formulation is in liquid or semisolid form.

4. A method of claim 3, wherein said formulation is a lotion, cream or ointment.

5. A method of claim 2, wherein said formulation comprises a water-in-oil emulsion.

6. A method of claim 2, wherein said formulation comprises an oil-in-water emulsion.

7. A method of claim 2, wherein the concentration of said acid, ester or salt in said formulation is 5–30% by weight based on the total weight of the formulation.

8. A method of claim 2, wherein an acid is administered and is pimelic acid, suberic acid, azelaic acid, sebacic acid, 1,9-nonanedicarboxylic acid, 1,10-decanedicarboxylic acid or 1,11-undecanedicarboxylic acid.

9. A method of claim 2, wherein a salt is administered and the acid component is pimelic acid, suberic acid, azelaic acid, sebacic acid, 1,9-nonanedicarboxylic acid, 1,10-decanedicarboxylic acid or 1,11-undecanedicarboxylic acid.

10. A method of claim 9, wherein the salt component is Na, K or a cation of an organic amine.

11. A method of claim 2, wherein a ester is administered and the acid component is pimelic acid, suberic acid, azelaic acid, sebacic acid, 1,9-nonanedicarboxylic acid, 1,10-decanedicarboxylic acid or 1,11-undecanedicarboxylic acid.

12. A method of claim 11, wherein the ester component is a 2,3-dihydroxypropyloxy radical.

13. A method of claim 8, wherein the acid is azelaic acid.

14. A method of claim 9, wherein the acid component is azelaic acid.

15. A method of claim 2, wherein a salt is administered and the acid component is pimelic acid, suberic acid, azelaic acid, sebacic acid, 1,9-nonanedicarboxylic acid, 1,10-decanedicarboxylic acid or 1,11-undecanedicarboxylic acid, the salt component is Na, K or a cation of an organic amine, and the formulation is an oil-in-water emulsion.

16. A method of claim 2, wherein an ester is administered and the acid component is pimelic acid, suberic acid, azelaic acid, sebacic acid, 1,9-nonanedicarboxylic acid, 1,10-decanedicarboxylic acid or 1,11-undecanedicarboxylic acid, the ester component is a 2,3-dihydroxypropyloxy radical, and the formulation is an oil-in-water emulsion.

17. A method of claim 8, wherein the concentration of said acid in said formulation is 5–30%.

18. A method of claim 9, wherein the concentration of said salt in said formulation is 5–30%.

19. A method of claim 2, wherein the formulation further comprises about 1–4% by weight of a keratolytically active substance.

20. A method of claim 19, wherein the keratolytically active substance is salicylic acid or resorcinol.

21. A method according to claim 1, wherein the keratoses are caused by prolonged exposure to the sun.

* * * * *